United States Patent
Fujimori

(10) Patent No.: US 11,304,598 B2
(45) Date of Patent: Apr. 19, 2022

(54) ENDOSCOPE SYSTEM AND METHOD OF MANUFACTURING IMAGE CAPTURING MODULE USED IN THE ENDOSCOPE SYSTEM

(71) Applicant: Olympus Corporation, Hachioji (JP)

(72) Inventor: Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 432 days.

(21) Appl. No.: 16/663,703

(22) Filed: Oct. 25, 2019

(65) Prior Publication Data

US 2020/0054201 A1 Feb. 20, 2020

Related U.S. Application Data

(63) Continuation of application No. PCT/JP2017/016718, filed on Apr. 27, 2017.

(51) Int. Cl.
*A61B 1/05* (2006.01)
*A61B 1/00* (2006.01)
*A61B 1/06* (2006.01)

(52) U.S. Cl.
CPC ............ *A61B 1/05* (2013.01); *A61B 1/00009* (2013.01); *A61B 1/00096* (2013.01); *A61B 1/00179* (2013.01); *A61B 1/06* (2013.01)

(58) Field of Classification Search
CPC ... A61B 1/05; A61B 1/00009; A61B 1/00096; A61B 1/00179; A61B 1/06;
(Continued)

(56) References Cited

U.S. PATENT DOCUMENTS

2010/0052192 A1 3/2010 Hasegawa et al.
2010/0085466 A1 4/2010 Fujimori et al.
(Continued)

FOREIGN PATENT DOCUMENTS

JP 2010-056170 3/2010
JP 2010091986 4/2010
(Continued)

OTHER PUBLICATIONS

International Search Report and Written Opinion from corresponding International Application No. PCT/JP2017/016718, dated Aug. 8, 2017.

*Primary Examiner* — Fernando Alcon
(74) *Attorney, Agent, or Firm* — Scully, Scott, Murphy & Presser, P.C.

(57) ABSTRACT

An image capturing module is used in an endoscope. The image capturing module comprises an image capturing portion having opposed surfaces defined by respective photodetection and reverse surfaces. The reverse surface includes external electrodes disposed thereon. A layered optical portion having a front surface to which light is applied and a rear surface that is opposite of the front surface. The layered optical portion having a plurality of optical members layered together. A layered device having a first principal surface with joint electrodes disposed thereon. A second principal surface opposes the first principal surface. The first principal surface is bonded to the reverse surface. The joint electrodes are joined to the external electrodes. The layered device includes a plurality of semiconductor devices layered together in which the first principal surface is larger in area than the photodetection surface and smaller in area than the rear surface.

15 Claims, 9 Drawing Sheets

(58) Field of Classification Search
CPC ....... A61B 1/0661; A61B 1/0684; A61B 1/07; A61B 1/0011; A61B 1/051
See application file for complete search history.

(56) References Cited

U.S. PATENT DOCUMENTS

| | | |
|---|---|---|
| 2010/0127341 A1 | 5/2010 | Kawazu et al. |
| 2010/0224767 A1* | 9/2010 | Kawano ................ G11B 7/22 |
| | | 257/435 |
| 2010/0271482 A1 | 10/2010 | Otsuki et al. |
| 2012/0008934 A1 | 1/2012 | Kawasaki |
| 2012/0184084 A1* | 7/2012 | Morikazu ............ B23K 26/40 |
| | | 257/E21.568 |
| 2012/0205766 A1* | 8/2012 | Takachi ............ H04N 9/04557 |
| | | 257/E31.127 |
| 2015/0295000 A1 | 10/2015 | Ishii et al. |
| 2017/0064249 A1* | 3/2017 | Kitano .................. A61B 1/051 |
| 2017/0248780 A1* | 8/2017 | Kitano .............. G02B 23/2423 |
| 2017/0251914 A1* | 9/2017 | Kitano ................ H04N 5/2257 |
| 2020/0054202 A1* | 2/2020 | Yamamoto ........... A61B 1/0011 |

FOREIGN PATENT DOCUMENTS

| | | |
|---|---|---|
| JP | 2010-258636 | 11/2010 |
| JP | 2012-018993 | 1/2012 |
| JP | 2015198805 | 11/2015 |
| JP | 2016150191 | 8/2016 |
| WO | 2008132980 | 11/2008 |
| WO | 2011055655 | 5/2011 |

* cited by examiner

ENDOSCOPE SYSTEM AND METHOD OF MANUFACTURING IMAGE CAPTURING MODULE USED IN THE ENDOSCOPE SYSTEM

CROSS-REFERENCE TO RELATED APPLICATION

This application is a continuation application of PCT Application No. PCT/JP 2017/016718 filed on Apr. 27, 2017, which is hereby incorporated by reference in its entirety.

TECHNICAL FIELD

The disclosed technology relates to an endoscope system having an image capturing module including a layered optical assembly, and a method of producing an image capturing module including a layered optical assembly.

DESCRIPTION OF THE RELATED ART

Attempts have been made to make endoscopes smaller in diameter for making them minimally invasive. Ultra-small-diameter endoscopes are required for insertion into ultra-small-diameter lumens such as blood vessels and bronchioles, for example. However, it is not easy to obtain ultra-small-diameter endoscopes having diameters smaller than 1.5 mm, for example, according to an extension of the technology to achieve smaller diameters for minimally invasive endoscopes.

Japanese Patent Application 2012-18993A or US Patent Application Publication No. 2012/0008934 discloses an image capturing module including a wafer-level layered body. The disclosed image capturing module is fabricated by joining a plurality of optical device wafers and an image capturing device wafer and thereafter cutting the joined wafers into individual pieces.

According to the above fabrication process, if the image capturing device wafer contains defective image capturing devices, then the manufactured image capturing modules include defective products. Therefore, it is preferable to cut an inspected image capturing device wafer and fabricate an image capturing module using only non-defective image capturing devices.

Furthermore, for use in endoscopes that are manufactured in small quantities and many types, it is preferable to simultaneously manufacture a plurality of image capturing modules including image capturing devices according to different specifications.

BRIEF SUMMARY OF EMBODIMENTS

The disclosed technology has been made in view of the foregoing.

One aspect of the disclosed technology is directed to an image capturing module used in an endoscope. The image capturing module comprises an image capturing portion having opposed surfaces defined by respective photodetection and reverse surfaces. The reverse surface includes external electrodes disposed thereon. A layered optical portion having a front surface to which light is applied and a rear surface that is opposite of the front surface. The rear surface is bonded to the photodetection surface. The layered optical portion having a plurality of optical members layered together. A layered device having a first principal surface with joint electrodes disposed thereon and a second principal surface that is opposite the first principal surface. The first principal surface is bonded to the reverse surface. The joint electrodes are joined to the external electrodes. The layered device includes a plurality of semiconductor devices layered together in which the first principal surface is larger in area than the photodetection surface and smaller in area than the rear surface.

Another aspect of the disclosed technology is directed to a method of manufacturing an image capturing module. The method comprises cutting an image capturing wafer to fabricate an image capturing portion having opposed surfaces defined by respective photodetection and reverse surfaces. The reverse surface includes external electrodes disposed thereon. Bonding the image capturing portion to a layered optical wafer having a plurality of optical wafers layered together. Cutting the layered optical wafer with the image capturing portion bonded thereto and fabricating an image capturing unit in which a layered optical portion includes a plurality of optical members layered together. The layered optical portion having a front surface and a rear surface that is opposite the front surface. The rear surface of the layered optical portion is bonded to the photodetection surface of the image capturing portion. The front surface is larger in area than the photodetection surface. The image capturing portion having a first aspect ratio $L1/W1$ equal to or smaller than 1.5 as a ratio between a length $L1$ thereof in optical axis directions and a width $W1$ thereof in directions perpendicular to the optical axis directions. The layered optical portion having a second aspect ratio $L2/W2$ equal to or larger than 2.0 as a ratio between a length $L2$ thereof in the optical axis directions and a width $W2$ thereof in the directions perpendicular to the optical axis directions.

A further aspect of the disclosed technology is directed to a method of manufacturing an image capturing module. The method comprises cutting an image capturing wafer to fabricate an image capturing portion having opposed surfaces defined by respective photodetection and reverse surfaces. The reverse surface includes external electrodes disposed thereon. Bonding the image capturing portion to a layered device wafer having a plurality of device wafers layered together. Cutting the layered device wafer with the image capturing portion bonded thereto and fabricating an image capturing unit in which a layered device includes a plurality of devices layered together. The layered device having a first principal surface and a second principal surface that is opposite the first principal surface. The rear surface of the image capturing portion is bonded to the first primary surface of the layered device. Bonding the photodetection surfaced of the image capturing unit to a layered optical wafer having a plurality of optical wafers layered together and cutting the layered optical wafer with the image capturing unit bonded thereto. Fabricating an image capturing module in which a layered optical portion includes a plurality of optical members layered together. The layered optical portion having a front surface to which light is applied and a rear surface that is opposite the front surface. The rear surface is bonded to the photodetection surface. The image capturing unit is bonded to the rear surface of the layered optical portion. The rear surface is larger in area than the photodetection surface and the first principal surface is larger in area than the photodetection surface and smaller in area than the rear surface.

In the method of manufacturing the image capturing module, the image capturing portion has a first aspect ratio $L1/W1$ equal to or smaller than 1.5 as a ratio between a length $L1$ thereof in optical axis directions and a width $W1$ thereof in directions perpendicular to the optical axis directions. The layered optical portion has a second aspect ratio L2/W2 equal to or larger than 2.0 as a ratio between a length L2 thereof in the optical axis directions and a width W2 thereof in the directions perpendicular to the optical axis directions. In the method of manufacturing the image capturing module of claim, the image capturing unit has a third aspect ratio L4/W1 equal to or smaller than 1.5 as a ratio between a length L4 thereof in the optical axis directions and the width W1 of a bonded surface of the image capturing portion in the directions perpendicular to the optical axis directions.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
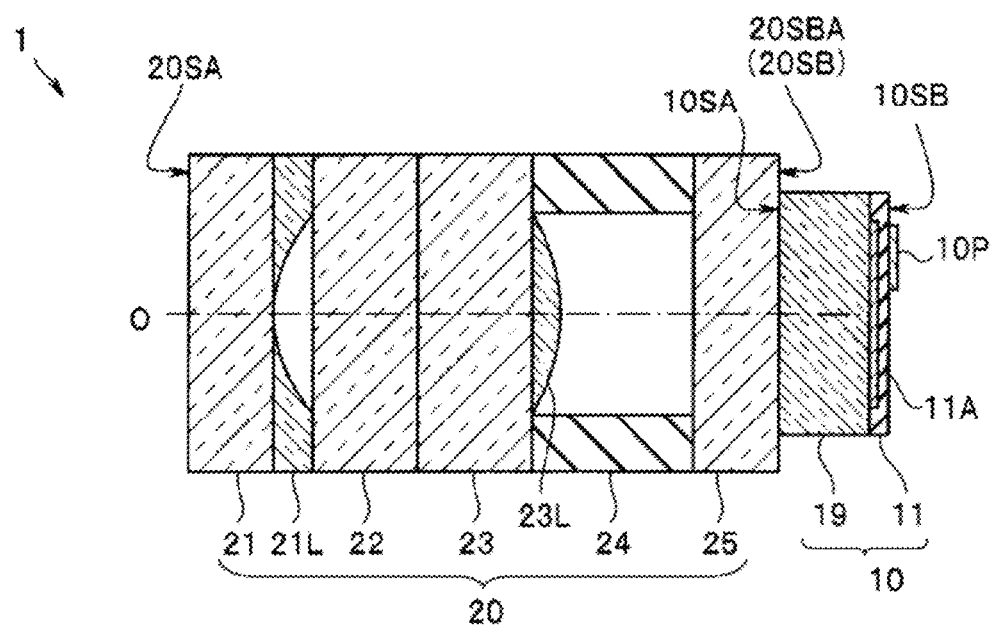
FIG. 1 is a cross-sectional view of an image capturing module according to a first embodiment.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of embodiments of the disclosed technology to provide an endoscope that is minimally invasive and easy to manufacture, an image capturing module that is ultra-small and easy to manufacture, and a method of manufacturing an image capturing module that is ultra-small and easy to manufacture.

According to an embodiment, there is provided an endoscope having an image capturing module, the image capturing module including an image capturing portion having a photodetection surface and a reverse surface that is opposite the photodetection surface, with external electrodes disposed on the reverse surface, and a layered optical portion having a front surface to which light is applied and a rear surface that is opposite the front surface, the rear surface being bonded to the photodetection surface, the layered optical portion including a plurality of optical members layered together, wherein the rear surface is larger in area than the photodetection surface, the image capturing portion having a first aspect ratio (L1/W1) equal to or smaller than 1.5 as a ratio between a length L1 thereof in optical axis directions and a width W1 thereof in directions perpendicular to the optical axis directions, the layered optical portion having a second aspect ratio (L2/W2) equal to or larger than 2.0 as a ratio between a length L2 thereof in the optical axis directions and a width W2 thereof in the directions perpendicular to the optical axis directions.

According to an embodiment, there is provided an image capturing module including an image capturing portion having a photodetection surface and a reverse surface that is opposite the photodetection surface, with external electrodes disposed on the reverse surface, and a layered optical portion having a front surface to which light is applied and a rear surface that is opposite the front surface, the rear surface being bonded to the photodetection surface, the layered optical portion including a plurality of optical members layered together, wherein the rear surface is larger in area than the photodetection surface, the image capturing portion having a first aspect ratio (L1/W1) equal to or smaller than 1.5 as a ratio between a length L1 thereof in optical axis directions and a width W1 thereof in directions perpendicular to the optical axis directions, the layered optical portion having a second aspect ratio (L2/W2) equal to or larger than 2.0 as a ratio between a length L2 thereof in the optical axis directions and a width W2 thereof in the directions perpendicular to the optical axis directions.

According to an embodiment, there is provided a method of manufacturing an image capturing module, including a first cutting step of cutting an image capturing wafer to fabricate an image capturing portion having a photodetection surface and a reverse surface that is opposite the photodetection surface, with external electrodes disposed on the reverse surface, a first bonding step of bonding the image capturing portion to a layered optical wafer having a plurality of optical wafers layered together, and a second cutting step of cutting the layered optical wafer with the image capturing portion bonded thereto, fabricating an image capturing unit in which a layered optical portion includes a plurality of optical members layered together, the layered optical portion having a front surface and a rear surface that is opposite the front surface, the rear surface of the layered optical portion being bonded to the photodetection surface of the image capturing portion, wherein the front surface is larger in area than the photodetection surface, the image capturing portion having a first aspect ratio (L1/W1) equal to or smaller than 1.5 as a ratio between a length L1 thereof in optical axis directions and a width W1 thereof in directions perpendicular to the optical axis directions, the layered optical portion having a second aspect ratio (L2/W2) equal to or larger than 2.0 as a ratio between a length L2 thereof in the optical axis directions and a width W2 thereof in the directions perpendicular to the optical axis directions.

According to the embodiments of the disclosed technology, there are provided an endoscope that is minimally invasive and easy to manufacture, an image capturing module that is ultra-small and easy to manufacture, and a method of manufacturing an image capturing module that is ultra-small and easy to manufacture.

First Embodiment

Figure 2:
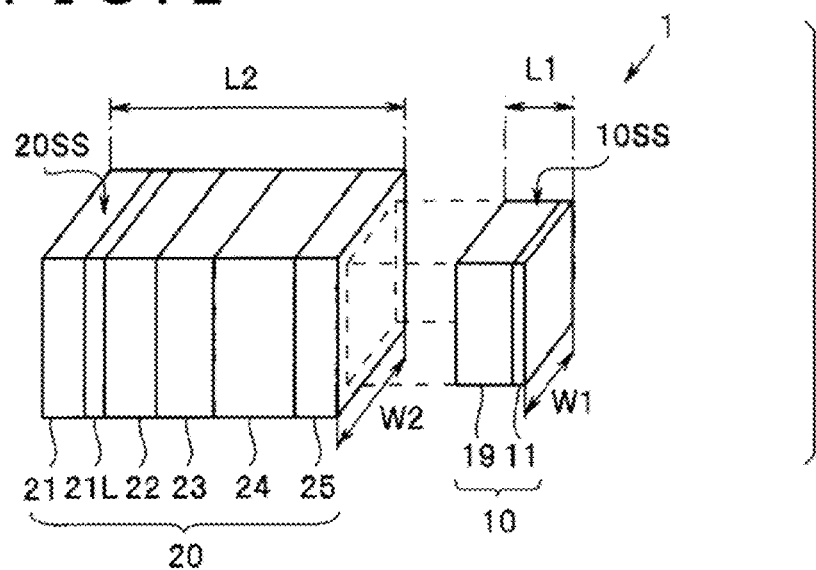
FIG. 2 is an exploded perspective view of the image capturing module according to the first embodiment.

As illustrated in FIGS. 1 and 2, an image capturing module 1 according to the present embodiment includes an image capturing portion 10 and a layered optical portion 20.

In the description that follows, figures based on various embodiments are schematic in nature. It should be noted that the relationships between thicknesses and widths of various parts and thickness ratios and relative angles between various parts are different from those in reality. Different figures may contain portions representing different dimensional relationships and ratios. In addition, some components and reference characters may be omitted from illustration.

The image capturing portion 10 includes an image capturing device 11 and a cover glass 19. As described later, the image capturing portion 10 is fabricated by cutting an image capturing wafer that has an image capturing device wafer including a plurality of image capturing devices 11 and a cover glass wafer bonded to the image capturing device wafer. Therefore, the image capturing portion 10, which is in the form of a first rectangular parallelepiped, has side surfaces 10SS as cut surfaces.

The cover glass 19 is not an indispensable component of the image capturing module 1. The image capturing portion 10 has a photodetection surface 10SA and a reverse surface 10SB that is opposite the photodetection surface 10SA. A plurality of external electrodes 10P are disposed on the reverse surface 10SB, i.e., an image capturing device reverse surface.

The image capturing device 11 has a photodetector 11A in the form of a CCD or CMOS image capturing unit. The photodetector 11A is connected to through interconnects (TSV: Through-Silicon Via). The image capturing device 11 may be either a front side illumination (FSI) image sensor or a back side illumination (BSI) image sensor. The photodetector 11A is connected to the external electrodes 10P through the through interconnects (not depicted).

The image capturing module 1 is of an ultra-small size specialized for endoscopes. The photodetection surface 10SA and the reverse surface 10SB, along a cross section perpendicular to an optical axis O, of the image capturing portion 10 are of a substantially square shape whose dimensions, or external dimensions, are equal to or less than a 1 mm square. The reverse surface 10SB whose cross-sectional dimensions are 600 μm×600 μm has a width W1 of 600 μm in directions perpendicular to the optical axis O. In a case where the reverse surface 10SB has a rectangular cross-sectional shape perpendicular to the optical axis O, the length of its longer sides is defined as the width.

The image capturing portion 10 has a length L1 of 300 μm, for example, in optical axis directions. In other words, a first aspect ratio that represents the ratio of the length L1 to the width W1 (L1/W1=300/600) is 0.5. If the first aspect ratio is equal to or smaller than 2.0, or preferably equal to or smaller than 1, then the image capturing portion 10 can stably be placed on a surface of auxiliary member with the photodetection surface 10SA facing down as a lower surface.

The layered optical portion 20 includes a plurality of optical members 21 through 25 layered together. The layered optical portion 20 has a front surface 20SA to which light is applied and a rear surface 20SB that is opposite the front surface 20SA. The rear surface 20SB of the layered optical portion 20 is bonded to the photodetection surface 10SA of the image capturing portion 10.

The optical members 21 and 23 are hybrid lens members as transparent members in the form of parallel flat plates with resin lenses 21L and 23L disposed respectively thereon. The optical member 22 is a filter in the form of a parallel flat plate made of an infrared cutoff material for removing infrared rays. The optical member 24 is a spacer having a through hole defined therein as an optical path. The optical member 24 may be of the same material as the resin lens 23L and may be formed at the same time as the resin lens 23L. The optical member 25 is a transparent member in the form of a parallel flat plate.

As described later, the layered optical portion 20, which is a wafer-level layered body, is in the form of a second rectangular parallelepiped having side surfaces 20SS as cut surfaces.

The layered optical portion 20 is of a substantially square shape whose dimensions, or external dimensions, are equal to or less than a 1 mm square. The rear surface 20SB or the front surface 20SA of the layered optical portion 20 is larger in area than the photodetection surface 10SA or the reverse surface 10SB of the image capturing portion 10. An effective optical path, or effective optics, at the front surface 20SA of the layered optical portion 20 is larger than an effective optical path at the rear surface 20SB, such that light introduced from the front surface 20SA is converged and emitted from the rear surface 20SB. The cross-sectional shape of the layered optical portion 20 that is perpendicular to the optical axis O may be a rectangular shape.

If the cross-sectional shape of the layered optical portion 20 in the directions perpendicular to the optical axis O is of dimensions 800 μm×800 μm, then the layered optical portion 20 has a width W2 of 800 μm in directions perpendicular to the optical axis O.

The width W2 of the layered optical portion 20 is larger than the width W1 of the image capturing portion 10. Therefore, the rear surface 20SB of the layered optical portion 20 includes a region 20SBA where the image capturing portion 10 is not bonded.

The layered optical portion 20 has a length L2 of 3000 μm, for example, in the optical axis directions. In other words, a second aspect ratio that represents the ratio of the length L2 to the width W2 (L2/W2=3000/800) is 3.75.

In order for the layered optical portion 20 to guarantee its optical characteristics, the length L2 is larger than the width W2. Therefore, the layered optical portion 20 is not easy to handle. For example, if the second aspect ratio is equal to or larger than 2.0, especially equal to or larger than 3.0, the layered optical portion 20 tends to fall over when placed on a surface of auxiliary member with the rear surface 20SB facing down as a lower surface.

The image capturing module 1 is ultra-small as the width W2 in the directions perpendicular to the optical axis O is equal to or smaller than 1 mm. However, as described later, the image capturing module 1 is fabricated according to a chip-on-wafer process in which an image capturing portion chip is bonded to a layered optical portion wafer including a plurality of layered optical portions 20. Therefore, the image capturing module 1 is easy to manufacture even though the second aspect ratio of the layered optical portion 20 is equal to or larger than 2.0. Although there is no particular upper limit specified for the second aspect ratio, the second aspect ratio should preferably be up to 10, for example, for shorter and smaller configurations.

Furthermore, since only those image capturing portions 10 which are determined as non-defective are used, the image capturing modules 1 are manufactured with a high yield.

Figure 3:
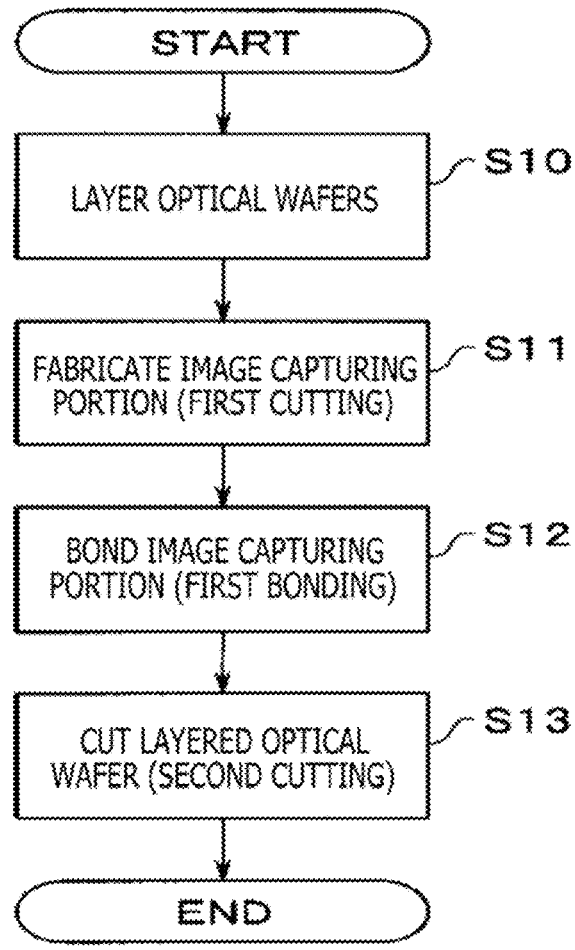
FIG. 3 is a flowchart illustrative of a method of manufacturing the image capturing module according to the first embodiment.

Method of Manufacturing the Image Capturing Module According to the First Embodiment A method of manufacturing the image capturing module 1 will be described below with reference to a flowchart of FIG. 3.

<Step S10> Optical Wafer Layering Step

Optical wafers 21W through 25W each having a plurality of optical members formed thereon are fabricated. For example, the optical wafers 21W, 23W, 25W are wafers in the form of parallel flat plates made of a transparent material. The optical wafer 22W is a filter wafer in the form of a parallel flat plate made of an infrared cutoff material for removing infrared rays. The filter wafer may be a transparent wafer or the like with a bandpass filter on a surface thereof for passing only light in a predetermined wavelength and cutting of light in unwanted wavelengths. The optical wafer 24W is a spacer wafer having a plurality of through holes defined therein as optical paths. The optical wafers 21W, 23W may be hybrid lens wafers with a plurality of resin lenses 21L and 23L disposed respectively thereon.

Figure 4:
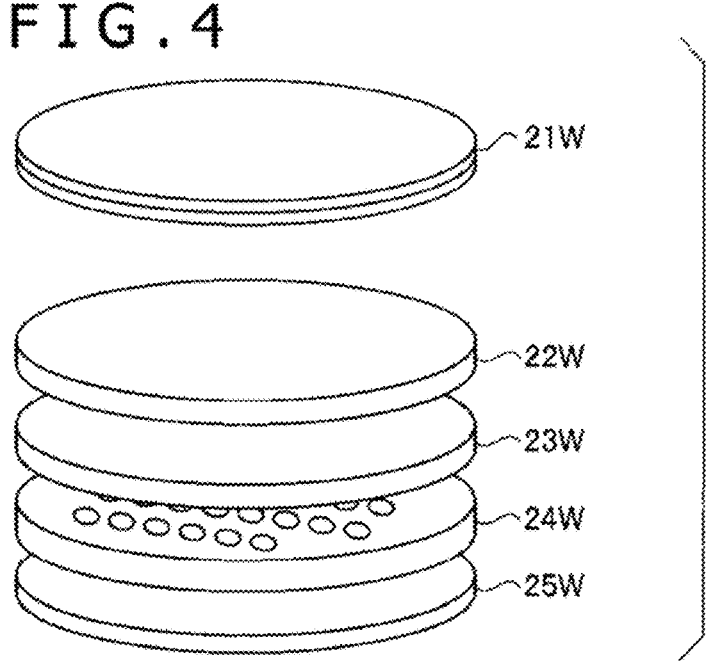
FIG. 4 is a perspective view illustrative of the method of manufacturing the image capturing module according to the first embodiment.

As illustrated in FIG. 4, the optical wafers 21W through 25W are bonded together by a transparent adhesive, not depicted, or joined directly together, producing a layered optical wafer 20W having a thickness of 3000 μm. The kinds, thicknesses, numbers, and layering order of the optical wafers may be appropriately changed.

<Step S11> Image Capturing Portion Fabricating Step First Cutting Step

A silicon wafer having a thickness ranging from 700 μm to 800 μm, for example, is processed by a known semiconductor fabrication process to fabricate an image capturing device wafer with a plurality of photodetectors 11A, etc. disposed thereon. The image capturing device wafer may include peripheral circuits for processing output signals from the photodetectors 11A according to a primary signal processing process and processing drive control signals.

In order to protect the photodetectors 11A on the image capturing device wafer, a cover glass wafer made of flat plate glass having a thickness of 250 μm, for example, is bonded to the image capturing device wafer, producing an image capturing wafer having a thickness of approximately 1000 μm. Then, the image capturing wafer is ground and polished on its reverse side until its thickness is reduced to 300 μm. Then, through interconnects connected to the photodetectors 11A and external electrodes 10P on the reverse surface 10SB are formed. The cover glass wafer is joined to and seals the entire surfaces of the photodetectors 11A to protect the photodetectors 11A. However, the cover glass wafer may be joined to and seal only the peripheries of the photodetectors 11A, forming air gaps, or spaces, in facing relation to the photodetectors 11A.

The image capturing wafer is then cut (first cutting step) into image capturing portions 10 each in the form of a square-shaped first rectangular parallelepiped having a thickness, i.e., a length L1 in the optical axis directions, of 300 μm and a width W1 of 600 μm. In other words, the first aspect ratio (L1/W1) between the length L1 in the optical axis directions and the width W1 in the directions perpendicular to the optical axis directions is 0.5.

It is preferable to conduct on a performance test on the image capturing devices 11 on the image capturing device wafer or the image capturing wafer and use only those image capturing portions 10 that are determined as non-defective in subsequent steps.

Step S11 (the image capturing portion fabricating step) may be carried out prior to step S10 (the optical wafer layering step).

<Step S12> Image Capturing Portion Bonding Step (First Bonding Step)

Figure 5:
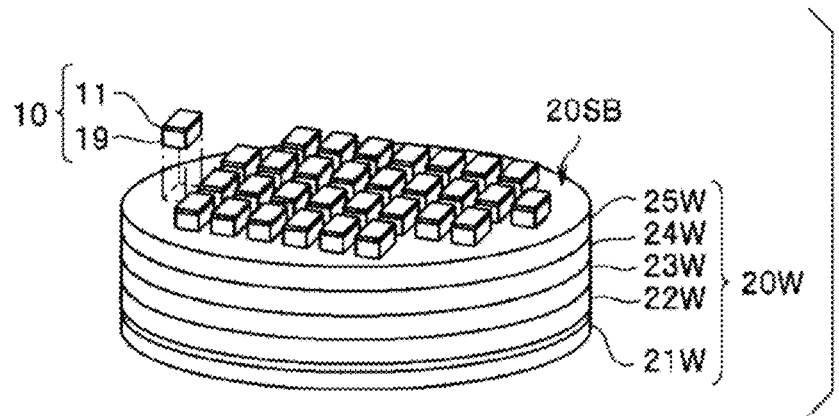
FIG. 5 is a perspective view illustrative of the method of manufacturing the image capturing module according to the first embodiment.

As illustrated in FIG. 5, the cover glasses 19 of a plurality of image capturing portions 10 that are determined as non-defective are bonded to the rear surface 20SB of the layered optical wafer 20W. The image capturing portions 10 whose first aspect ratio is 0.5 can stably be placed on the layered optical wafer 20W with their photodetection surface 10SA facing down as lower surfaces. If the first aspect ratio is equal to or smaller than 1.5, preferably equal to or smaller than 1.0, then the image capturing portions 10 can easily be placed on the layered optical wafer 20W. The plurality of image capturing portions 10 are placed with clearances of 410 μm, for example, left therebetween.

<Step S13> Layered Optical Wafer Cutting Step (Second Cutting Step)

Figure 6:
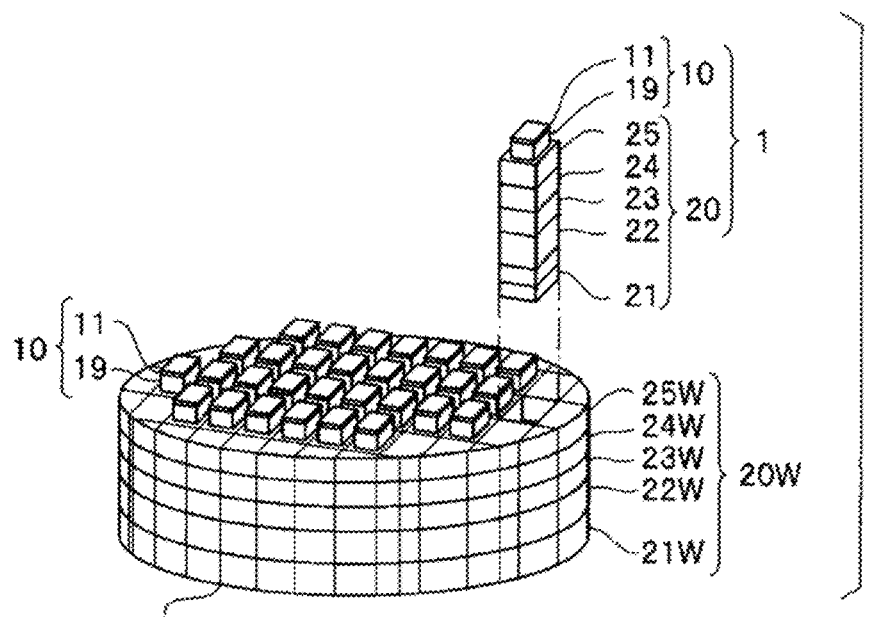
FIG. 6 is a perspective view illustrative of the method of manufacturing the image capturing module according to the first embodiment.

As illustrated in FIG. 6, the layered optical wafer 20W with the plurality of image capturing portions 10 bonded thereto is cut along cutting lines CL, each having a width of 10 μm, along the side faces of the image capturing portions 10, producing image capturing modules 1. The manufacturing method according to the present embodiment uses a dicing blade in the cutting step. However, an etching process, a process using a laser, or the like may be used as long as it can divide the layered optical wafer 20W.

Each of the image capturing modules 1 fabricated in the second cutting step includes an image capturing portion 10 in the form of a first rectangular parallelepiped and a layered optical portion 20 in the form of a second rectangular parallelepiped.

As already described, if the outer dimension, or the width W2, is equal to or smaller than 1 mm and the second aspect ratio is equal to or larger than 2.0, then the layered optical portion 20 is not easy to handle and is difficult to bond to the image capturing portion 10.

However, the image capturing modules 1 are fabricated according to the chip-on-wafer process in which the image capturing portions 10 as chips are disposed on the layered optical wafer 20W. Therefore, the image capturing modules 1 are ultra-small with their width being equal to smaller than 1 mm, and are easy to fabricate even if the second aspect ratio of the layered optical portions 20 is of a large value of 3.75. Furthermore, since only those image capturing portions 10 which are determined as non-defective are used, the image capturing modules 1 are manufactured with a high yield.

Inasmuch as the image capturing module 1 is fabricated according to the chip-on-wafer process, the width W2 (800 μm) of the sectional surfaces, i.e., the front surface 20SA and the rear surface 20SB, lying in the directions perpendicular to the optical axis directions, of the layered optical portion 20 is larger than the width W1 (600 μm) of the sectional surfaces i.e., the photodetection surface 210SA and the reverse surface 10SB, lying in the directions perpendicular to the optical axis directions, of the image capturing portion 10.

Modifications of the First Embodiment

An image capturing module 1A according to a modification of the first embodiment is similar to the image capturing module 1 and offers the same advantages as the image capturing module 1, those components which have same functions are denoted by identical reference characters and will not be described below.

The layered optical portion 20 of the image capturing module 1 is in the form of a complete rectangular parallelepiped. However, the term "rectangular parallelepiped" according to the disclosed technology covers approximate rectangular parallelepipeds that have corners beveled or curved.

The layered optical portion 20 has an optical axis whose cross-sectional shape is circular in the directions perpendicular to the optical axis directions. Because the layered optical portion 20 has the largest external dimensions, the layered optical portion 20 in particular should preferably be in the form of an approximate rectangular parallelepiped whose corners are beveled or curved.

Figure 7A:
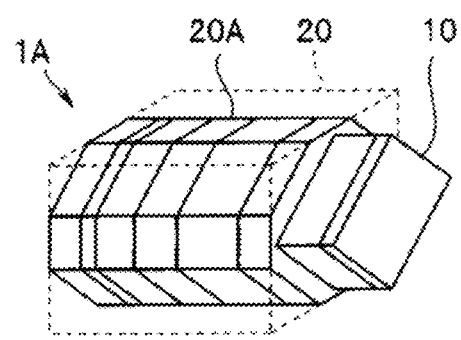
FIG. 7A is a perspective view of an image capturing module according to a modification of the first embodiment.
Figure 7B:
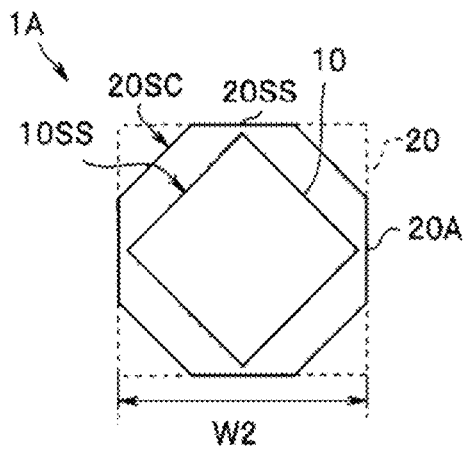
FIG. 7B is a rear elevational view of the image capturing module according to the modification of the first embodiment.

The image capturing module 1A illustrated in FIGS. 7A and 7B includes a layered optical portion 20A that is in the form of an octagonal prism whose corners parallel to the optical axis outside of the optical path are beveled.

The image capturing module 1A is smaller in diameter than the image capturing module 1 as the layered optical portion 20A that has the largest external dimensions is beveled and has the external dimensions reduced. A beveling step is performed on the layered optical portion 20A after the layered optical wafer has been cut into image capturing modules 1A.

Moreover, the side surfaces loss of the image capturing portion 10 of the image capturing module 1A are disposed parallel to beveled surfaces 20SC of the layered optical portion 20A. Specifically, in the image capturing portion bonding step illustrated in FIG. 5, the plurality of image capturing portions 10 are disposed with their corners facing each other, and in the layered optical wafer cutting step illustrated in FIG. 6, the layered optical wafer is cut along cutting lines CL that are inclined at 45 degrees to the side surfaces of the image capturing portions 10. Therefore, in the image capturing module 1A, the image capturing portion 10 is bonded, as turned by 45 degrees with respect to the layered optical portion 20A, to the layered optical portion 20A.

As illustrated in FIG. 7B, the layered optical portion 20A of the image capturing module 1A is beveled. The distance between inner peripheral edges of the layered optical portion 20A and outer peripheral edges of the image capturing portion 10 is essentially constant, making it easy to bevel the layered optical portion 20A.

Figure 7C:
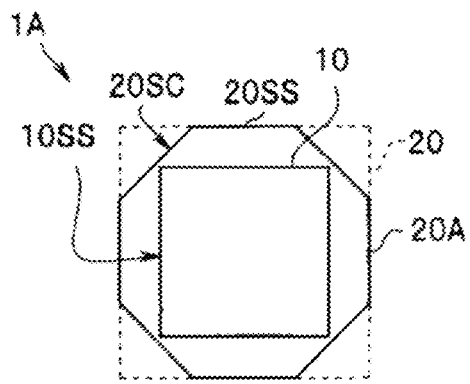
FIG. 7C is a rear elevational view of an image capturing module according to a modification of the first embodiment.

As illustrated in FIG. 7C, in the image capturing module 1A, the corners, parallel to the optical axis, of the layered optical portion 20A are beveled, and the side surfaces 10SS of the image capturing portion 10 may be disposed so as to cross at 45 degrees the beveled surfaces 20SC of the layered optical portion 20A.

Specifically, in the image capturing portion bonding step illustrated in FIG. 5, the plurality of image capturing portions 10 are disposed with their sides facing each other, and in the layered optical wafer cutting step illustrated in FIG. 6, the layered optical wafer is cut along cutting lines CL that are parallel to the side surfaces loss of the image capturing portions 10. Therefore, in the image capturing module 1A, the image capturing portion 10 is bonded, as not turned with respect to the layered optical portion 20A, to the layered optical portion 20A. The beveling process illustrated in FIG. 7C allows a larger number of image capturing portions 10 to be placed on the layered optical wafer 20W, compared with the beveling process illustrated in FIG. 7B.

The width W2 of the layered optical portion 20A represents the width of the layered optical portion 20 in the form of a rectangular parallelepiped before it is beveled.

Second Embodiment

An image capturing module 1B according to a second embodiment is similar to the image capturing module 1 and offers the same advantages as the image capturing module 1, those components which have same functions are denoted by identical reference characters and will not be described below.

Figure 8:
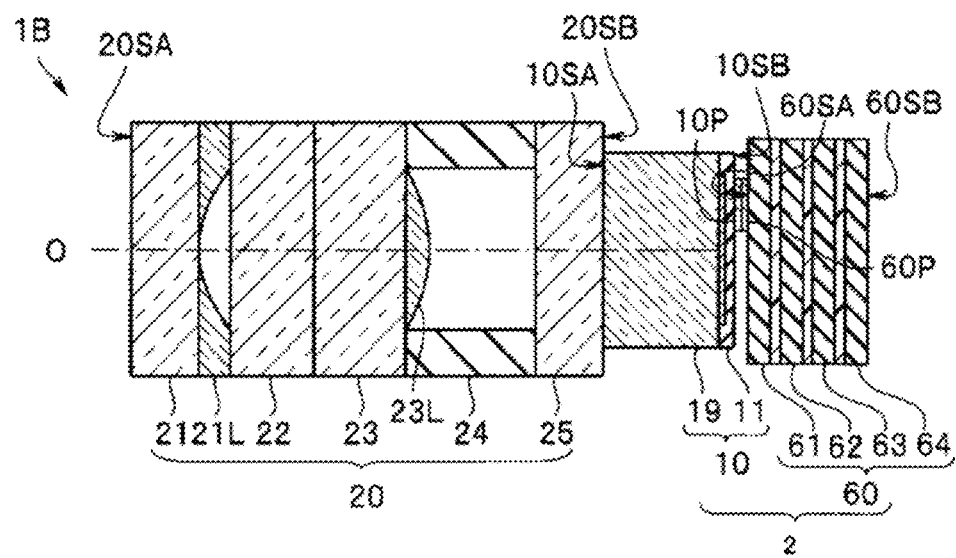
FIG. 8 is a cross-sectional view of an image capturing module according to a second embodiment.
Figure 9:
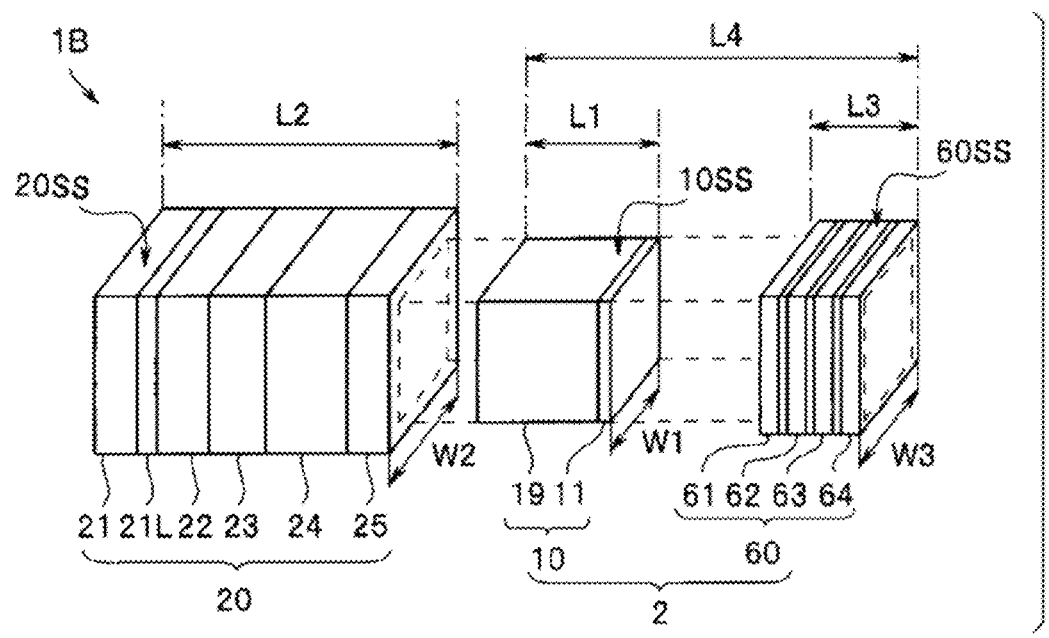
FIG. 9 is a perspective view of the image capturing module according to the second embodiment.

As illustrated in FIGS. 8 and 9, the image capturing module 1B according to the second embodiment includes the image capturing portion 10, the layered optical portion 20, and a layered device 60 having a plurality of semiconductor devices 61 through 64 layered together.

The layered device 60 has a first principal surface 60SA and a second principal surface 60SB that is opposite the first principal surface 60SA. The layered device 60 is in the form of a third rectangular parallelepiped fabricated by cutting a layered device wafer 60W (see FIG. 11) and having side surfaces 60SS as cut surfaces.

The layered device 60 includes joint electrodes 60P disposed on the first principal surface 60SA and joined to the external electrodes 10P on the reverse surface 10SB of the image capturing portion 10. The layered device 60 has a length L3 of 200 μm in the optical axis directions and a width W3 of 700 μm in the directions perpendicular to the optical axis.

The semiconductor devices 61 through 64 process an image signal output from the image capturing device 11 according to a primary image processing process and also process control signals for controlling the image capturing device 11. The semiconductor devices 61 through 64 each include an analog-to-digital converting circuit, a memory, a transmission output circuit, a filter circuit, thin-film capacitors, thin-film inductors, etc. The number of devices included in the layered device 60 ranges from 3 to 10. The semiconductor devices 61 through 64 are electrically connected to each other by through interconnects, not depicted.

The image capturing module 1B is fabricated by two on-chip wafer steps, i.e., a double on-chip wafer step. Specifically, a method of manufacturing the image capturing module 1B includes a first on-chip wafer step in which a plurality of image capturing portions 10 are electrically joined to a layered device wafer 60W (see FIG. 11) and bonded thereto, and the assembly is cut into image capturing units 2. The method also includes a second on-chip wafer step in which the image capturing units 2 as chips that include image capturing portions 10 and layered devices 60 are bonded to the layered optical wafer 20W and the assembly is cut into image capturing modules 1B.

The first principal surface 60SA is larger than the photodetection surface 10SA and the reverse surface 10SB of the image capturing portion 10 and smaller than the front surface 20SA and the rear surface 20SB of the layered optical portion 20. In other words, the width W3 of the first principal surface 60SA that is of a square shape is larger than the width W1 of the photodetection surface 10SA and smaller than the width W2 of the front surface 20SA.

For example, the width W1 of the photodetection surface 10SA of the image capturing portion 10 is 600 μm. The width W2 of the front surface 20SA of the layered optical portion 20 is 800 μm. The width W3 of the first principal surface 60SA of the layered device 60 is 700 μm.

Since the image capturing module 1B includes the small-size layered device 60 for processing an image signal according to a primary signal processing process, the image capturing module 1B is of higher performance than the image capturing module 1 while being of substantially the same size as the image capturing module 1.

Figure 10:
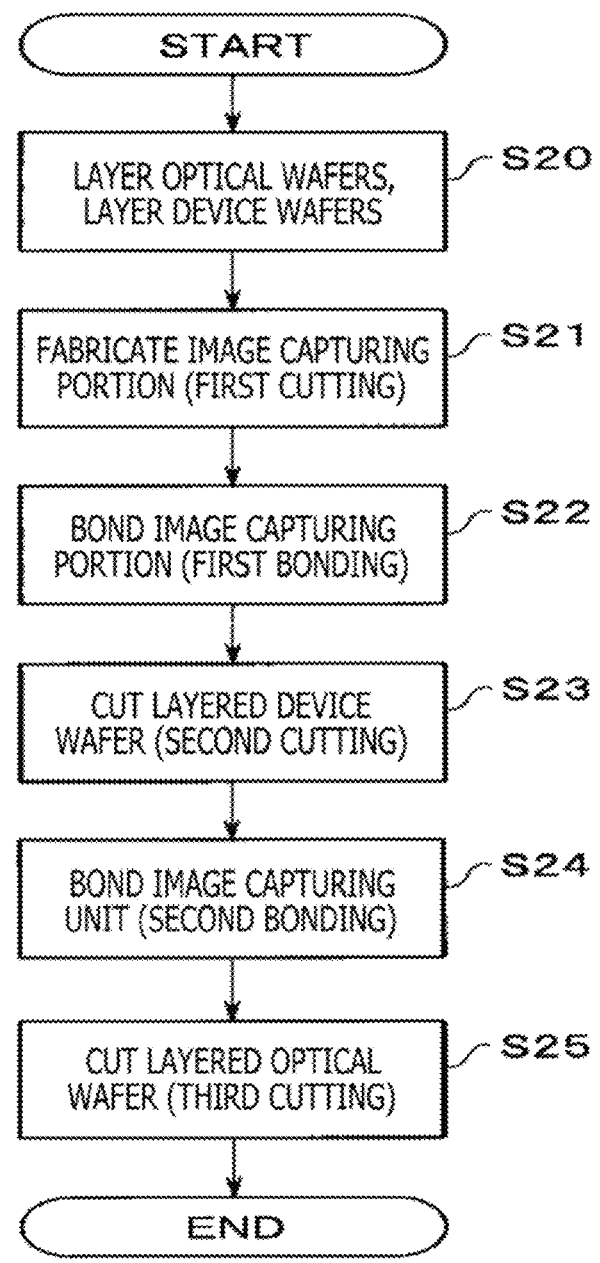
FIG. 10 is a flowchart illustrative of a method of manufacturing the image capturing module according to the second embodiment.

Method of Manufacturing the Image Capturing Module According to the Second Embodiment A method of manufacturing the image capturing module 1B will be described below with reference to a flowchart of FIG. 10.

<Step S20> Optical Wafer Layering Step/Device Wafer Layering Step

An optical wafer layering step is the same as step S10 according to the first embodiment and will not be described below.

Device wafers 61W through 64W (see FIG. 11) each having a plurality of semiconductor devices formed thereon are fabricated. The device wafers 61W through 64W each include a plurality of semiconductor devices 61 through 64 such as analog-to-digital converting circuits, memories, transmission output circuits, filter circuits, thin-film capacitors, thin-film inductors, etc.

In a device wafer layering step, the device wafers 61W through 64W are layered together, and their through interconnects, not depicted, are joined together. The device wafers 61W through 64W are bonded together by a sealing resin, not depicted, producing the layered device wafer 60W (see FIG. 11). The layered device wafer 60W has a thickness of 300 μm.

<Step S21> Image Capturing Portion Fabricating Step (First Cutting Step)

A first cutting step in which an image capturing wafer is cut to fabricate image capturing portions each having a photodetection surface and a reverse surface that is opposite the photodetection surface and having external electrodes disposed thereon, is the same as step S11 according to the first embodiment, and will not be described below.

<Step S22> Image Capturing Portion Bonding Step (First Bonding Step)

Figure 11:
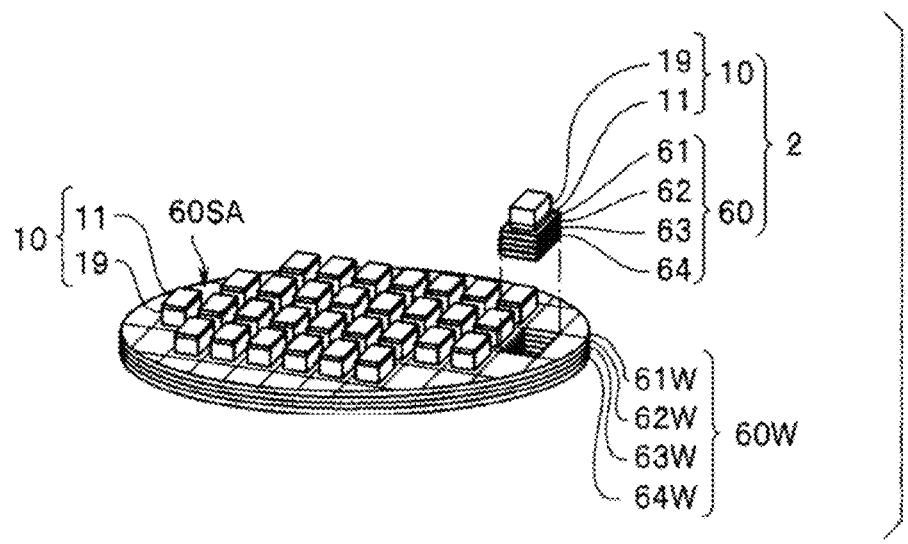
FIG. 11 is a perspective view illustrative of the method of manufacturing the image capturing module according to the second embodiment.

As illustrated in FIG. 11, a plurality of image capturing portions 10 are bonded to the first principal surface 60SA of the layered device wafer 60W that includes the plurality of device wafers 61W through 64W layered together. The image capturing portions 10 have the image capturing devices 11 bonded to the layered device wafer 60W. The plurality of image capturing portions 10 are placed with clearances of 210 μm, for example, left therebetween. Since the first aspect ratio of the image capturing portions 10 is 0.5 smaller than 1.5, the image capturing portions 10 can easily be placed on the layered device wafer 60W.

<Step S23> Layered Device Cutting Step (Second Cutting Step)

As illustrated in FIG. 11, the layered device wafer 60W with the plurality of image capturing portions 10 bonded thereto is cut along cutting lines CL, each having a width of 10 μm, along the clearances between the image capturing portions 10, producing image capturing units 2.

Each of the image capturing units 2 includes an image capturing portion 10 having an image capturing device 11 bonded to a layered device 60 in the form of a third rectangular parallelepiped including a plurality of devices 61 through 64 layered together. The width W3 of the first principal surface 60SA or the second principal surface 60SB of the layered device 60 is 700 μm, and the thickness of the layered device 60, i.e., the length L3 in the optical axis directions, is 200 μm.

<Step S24> Image Capturing Unit Bonding Step (Second Bonding Step)

Figure 12:
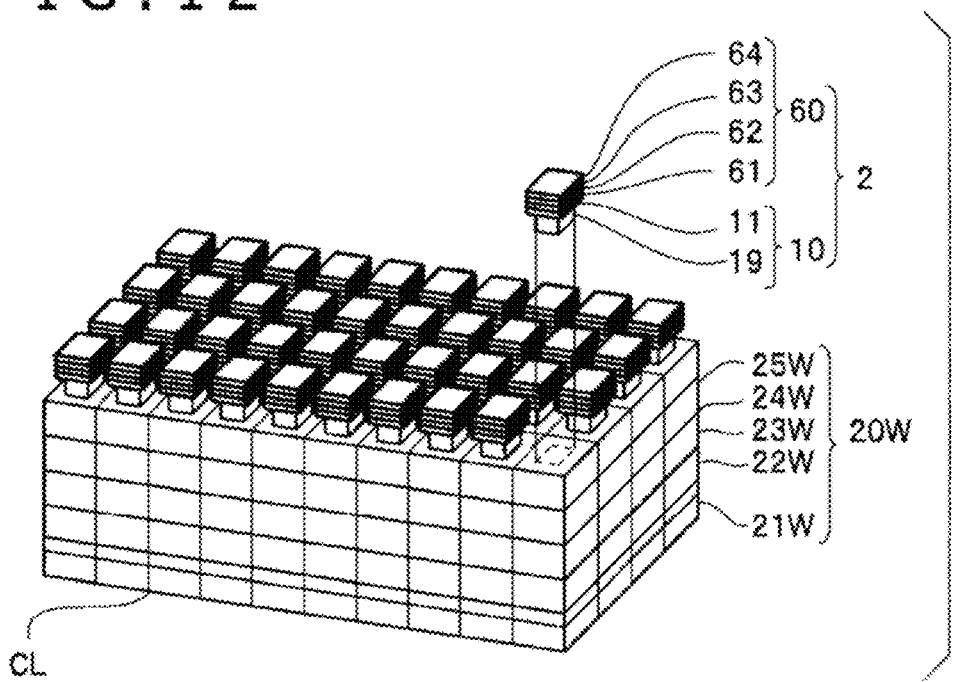
FIG. 12 is a perspective view illustrative of the method of manufacturing the image capturing module according to the second embodiment.

As illustrated in FIG. 12, the photodetection surfaces 10SA of the image capturing units 2 are bonded to the layered optical wafer 20W that include a plurality of optical wafers 21W through 25W layered together. As illustrated in FIG. 12, the optical wafer 21W, etc. are not circular wafers, but rectangular wafers. The wafers according to the disclosed technology, i.e., the layered optical wafer 20W and the layered device wafer 60W, may be either circular wafers or rectangular wafers.

The bonded surface of the image capturing unit 2 has a width that is the same as the width W1 of 600 μm of the image capturing device 11 in the directions perpendicular to the optical axis directions. The image capturing unit 2 has a thickness, i.e., a length L4 in the optical axis directions, of 500 μm that is the sum of the length L1 of 300 μm of the image capturing portion and the length L3 of 200 μm of the layered device 60. Since the image capturing unit 2 has a third aspect ratio (L4/W1), as the ratio between the length L4 and the width W1 of the bonded surface, of 0.83 (=500/600) smaller than 1.5, the image capturing unit 2 can easily be placed on the layered optical wafer 20W. The plurality of image capturing units 2 are placed with clearances of 210 μm, for example, left therebetween.

<Step S25> Layered Optical Wafer Cutting Step (Third Cutting Step)

As illustrated in FIG. 12, the layered optical wafer 20W with the image capturing units 2 bonded thereto is cut along cutting lines CL, each having a width of 10 μm, along the clearances between the image capturing units 2, producing image capturing modules 1B.

As illustrated in FIG. 8, each image capturing module 1B includes a layered optical portion 20 in the form of a second rectangular parallelepiped including a plurality of optical members 21 through 25 layered together, and an image capturing unit 2 bonded to a rear surface 20SB of the layered optical portion 20.

In the image capturing module 1B fabricated according to the two on-chip wafer steps, i.e., the double on-chip wafer step, the width W1 of the photodetection surface 10SA of the image capturing portion 10 is 600 μm, the width W2 of the front surface 20SA of the layered optical portion 20 is 800 μm, and the width W3 of the first principal surface 60SA of the layered device 60 is 700 μm. In other words, the member that is finally cut off has the largest area.

Particularly, in each of the two on-chip wafer steps, a plurality of chips whose aspect ratio is equal to or smaller than 1.5, preferably equal to or smaller than 1.0, are bonded to a wafer. Therefore, the method of manufacturing the image capturing module according to the present embodiment is easy to perform.

The layered optical portion 20 of the image capturing module 1B may be beveled in the same manner as with the image capturing module 1A, offering the same advantages as with the image capturing module 1A.

Third Embodiment

Figure 13:
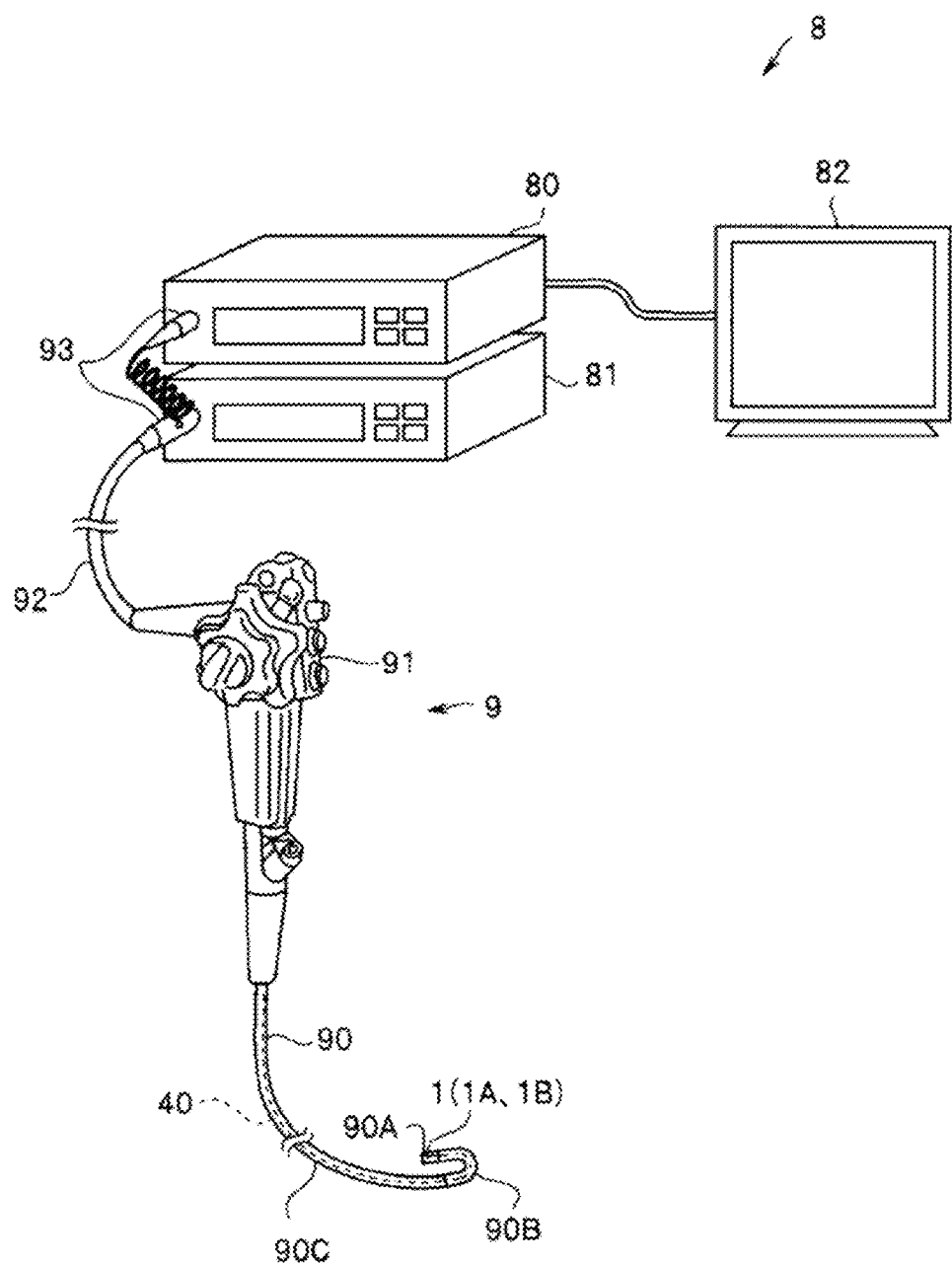
FIG. 13 is a perspective view of an endoscopic system including an endoscope according to a third embodiment.

As illustrated in FIG. 13, an endoscopic system 8 including an endoscope 9 according to the present embodiment includes the endoscope 9, a processor 80, a light source device 81, and monitor 82. The endoscope 9 has an insertion portion 90, an operating portion 91, and a universal cord 92. The endoscope 9 is inserted into a body cavity in an examinee, captures intracorporeal images of the examinee, and outputs image signals.

The insertion portion 90 includes a distal-end portion 90A incorporating an image capturing module 1, 1A, or 1B (hereinafter referred to as "image capturing module 1, etc." disposed therein, a bendable portion 90B joined to a proximal-end side of the distal-end portion 90A and freely bendable, and a soft portion 90C joined to a proximal-end side of the bendable portion 90B. The bendable portion 90B can be bent by an operation of the operating portion 91. The endoscope 9 may be a rigid endoscope or a capsule-type endoscope.

The operating portion 91 that has various buttons, etc. for operating the endoscope 9 is disposed on a proximal-end side of the insertion portion 90 of the endoscope 9.

The light source device 81 has a white LED, for example. Illumination light that is emitted by the light source device 81 is guided through a light guide not, that extends through the universal cord 92 and the insertion portion 90 to the distal-end portion 90A, illuminating a subject.

The endoscope 9 has the insertion portion 90, the operating portion 91, and the universal cord 92. An image signal that is output from the image capturing module 1, etc. disposed in the distal-end portion 90A of the insertion portion 90 is transmitted through a signal cable 40 extending through the insertion portion 90.

Since the image capturing module 1, etc. is ultra-small, the endoscope 9 is minimally invasive with the distal-end portion 90A of the insertion portion 90 being of a small diameter of less than 1.5 mm. The image capturing module 1, etc. is easy to manufacture though it includes the layered optical portion 20 having a high aspect ratio. Furthermore, inasmuch as the image capturing module 1B includes an integral peripheral circuit for processing an output signal from the image capturing portion 10 according to a primary signal processing process and processing drive control signals, the endoscope 9 using the image capturing module 1B is easy to manufacture and has good image quality performance.

Modifications of the Third Embodiment

As endoscopes according to modifications of the endoscope 9 according to the third embodiment are similar to the endoscope 9 and offer the same advantages as those of the endoscope 9, those components which have same functions are denoted by identical reference characters and will not be described below. Though the endoscopes will be described by way of example, the modifications may be applied to image capturing modules for use in applications other than endoscopes.

Modification 1 of the Third Embodiment

Figure 14:
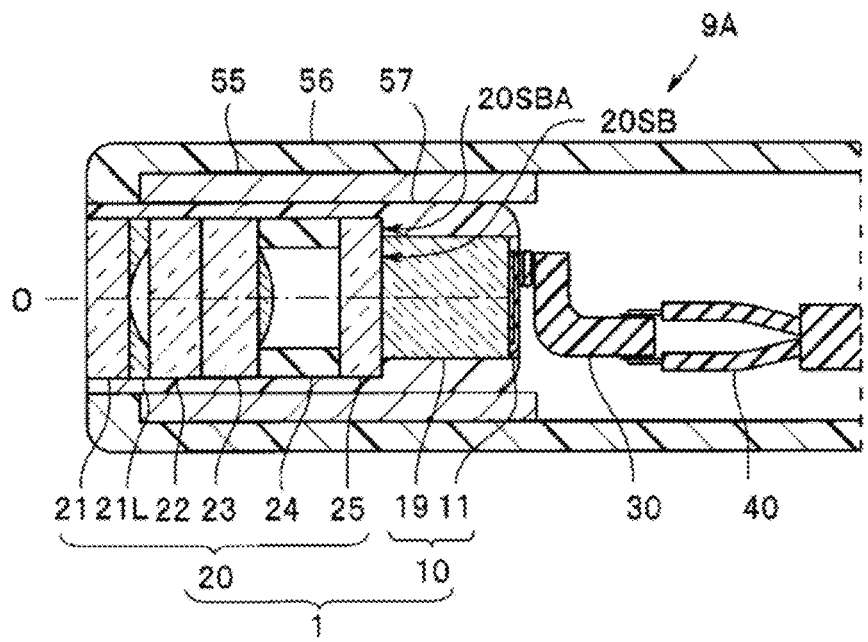
FIG. 14 is a cross-sectional view of a distal-end portion of an endoscope according to modification 1 of the third embodiment.

As illustrated in FIG. 14, an image capturing module 1 inserted in a through hole in a frame member 55 of an endoscope 9A according to modification 1 includes a light shield resin 57 disposed as auxiliary member on a region 20SBA, to which the image capturing portion 10 is not bonded, of a rear surface 20SB of a layered optical portion 20 and covering side surfaces of the layered optical portion 20. The frame member 55 is covered with an outer covering 56.

As the rear surface 20SB of the layered optical portion 20 is larger in area than the image capturing portion 10, the light shield resin 57 can be placed in position without an increase in the diameter of the distal-end portion 90A of the endoscope 9A. Thus, the image capturing module 1 of the endoscope 9A is highly reliable and is of high performance because noise due to ambient light and water are prevented from entering the image capturing module 1 from the side surfaces of the image capturing device 11. Image capturing modules that are of the same structure as the endoscope 9A and that include the light shield resin 57 offer the same advantages as those of the endoscope 9A.

Modification 2 of the Third Embodiment

Figure 15:
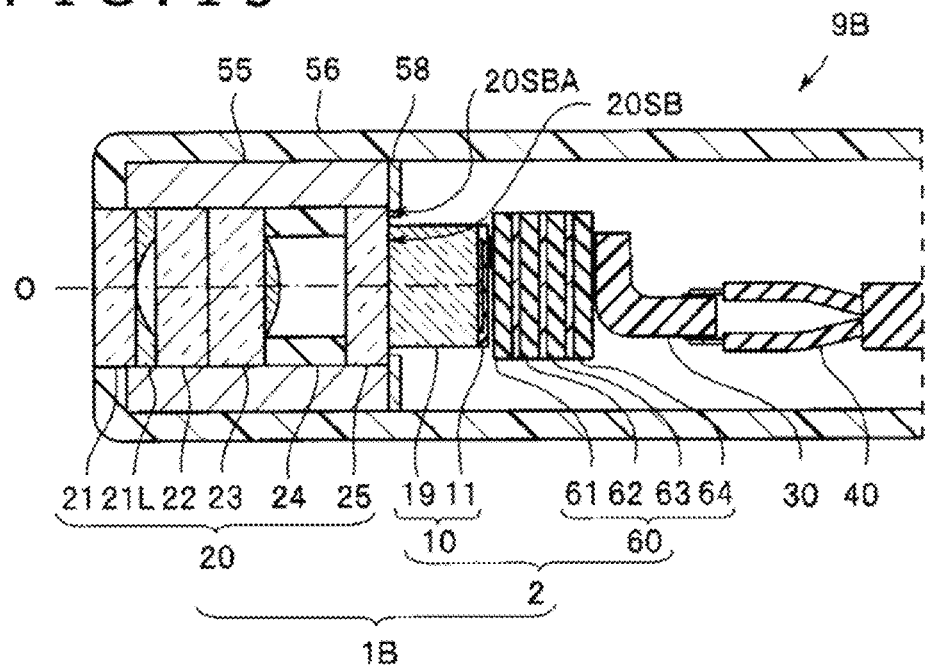
FIG. 15 is a cross-sectional view of a distal-end portion of an endoscope according to modification 2 of the third embodiment.

As illustrated in FIG. 15, an image capturing module 1B inserted in a through hole in a frame member 55 of an endoscope 9B according to modification 2 includes a convex portion 58, as auxiliary member, of a wall surface of the frame member 55, disposed on a region 20SBA, to which the image capturing portion 10 is not bonded, of a rear surface 20SB of a layered optical portion 20. The frame member 55 is a component of the distal-end portion 90A, and may have a through hole in which an illumination optical system is inserted, in addition to the insertion hole in which the image capturing module 1B is inserted.

The convex portion 58 may be a plurality of screws or the like inserted into the frame member 55 from an outer surface thereof, and function as positioning members for positioning the image capturing module 1B in the optical axis directions.

The image capturing module 1B in which the rear surface 20SB of the layered optical portion 20 is larger in area than the image capturing portion 10 allows the convex portion 58 to be placed in position in abutment against the region 20SBA of the rear surface 20SB of the layered optical portion 20 without an increase in the diameter of the distal-end portion 90A of the endoscope 9A. The image capturing module 1B in which the convex portion 58 can define the position of the frame member 55 in the optical axis directions is easy to be manufacture. Image capturing modules that are of the same structure as the endoscope 9B and that include the frame member 55 including the convex portion 58 offer the same advantages as those of the endoscope 9B.

The endoscope according to modification 1 may have the image capturing module 1A or 1B, and the endoscope according to modification 2 may have the image capturing module 1 or 1A.

The disclosed technology is not limited to the embodiments and the modifications, etc. described above, but various changes, combinations, and applications of the embodiments may be made without departing from the scope of the invention.

In sum, one aspect of the disclosed technology is directed to an image capturing module used in an endoscope. The image capturing module comprises an image capturing portion having opposed surfaces defined by respective photodetection and reverse surfaces. The reverse surface includes external electrodes disposed thereon. A layered optical portion having a front surface to which light is applied and a rear surface that is opposite of the front surface. The rear surface is bonded to the photodetection surface. The layered optical portion having a plurality of optical members layered together. A layered device having a first principal surface with joint electrodes disposed thereon and a second principal surface that is opposite the first principal surface. The first principal surface is bonded to the reverse surface. The joint electrodes are joined to the external electrodes. The layered device includes a plurality of semiconductor devices layered together in which the first principal surface is larger in area than the photodetection surface and smaller in area than the rear surface.

The rear surface is larger in area than the photodetection surface. The image capturing portion having a first aspect ratio L1/W1 equal to or smaller than 1.5 as a ratio between a length L1 thereof in optical axis directions and a width W1 thereof in directions perpendicular to the optical axis directions. The layered optical portion having a second aspect ratio L2/W2 equal to or larger than 2.0 as a ratio between a length L2 thereof in the optical axis directions and a width W2 thereof in the directions perpendicular to the optical axis directions. The rear surface is larger in area than the photodetection surface. The image capturing portion having a first aspect ratio L1/W1 equal to or smaller than 1.5 as a ratio between a length L1 thereof in optical axis directions and a width W1 thereof in directions perpendicular to the optical axis directions.

The layered optical portion includes a second aspect ratio L2/W2 equal to or larger than 2.0 as a ratio between a length L2 thereof in the optical axis directions and a width W2 thereof in the directions perpendicular to the optical axis directions. The layered optical portion has first side surfaces being defined as first cut surfaces. The rear surface is larger in area than the photodetection surface. The image capturing portion includes a first aspect ratio L1/W1 as a ratio between a length L1 thereof in optical axis directions and a width W1 thereof in directions perpendicular to the optical axis directions. A third aspect ratio L4/W1 as a ratio between a length L4 of an image capturing unit including the image capturing portion and the layered device, in the optical axis directions and the width W1 of the image capturing portion in the directions perpendicular to the optical axis directions.

Each of the first aspect ratio and the third aspect ratio is equal to or smaller than 1.5. The layered optical portion having a second aspect ratio L2/W2 equal to or larger than 2.0 as a ratio between a length L2 thereof in the optical axis directions and a width W2 thereof in the directions perpendicular to the optical axis directions. The layered optical portion has first side surfaces being defined as first cut surfaces and the layered device has second side surfaces being defined as second cut surfaces. The layered optical portion has corners substantially parallel to an optical axis thereof in which the corners are beveled. The image capturing portion has third side surfaces disposed substantially parallel to beveled surfaces of the layered optical portion. The layered optical portion has corners substantially parallel to an optical axis thereof in which the corners being beveled.

The image capturing portion has third side surfaces disposed so as to cross at approximately 45 degrees to beveled surfaces of the layered optical portion. An auxiliary member is disposed on a region to which the image capturing portion is not bonded of the rear surface of the layered optical portion. The auxiliary member comprises a light shield resin covering side surfaces of the layered optical portion. The image capturing module further comprises a frame member having a through hole in which the image capturing module is inserted. The auxiliary member includes a convex portion of a wall surface of the through hole.

Another aspect of the disclosed technology is directed to a method of manufacturing an image capturing module. The method comprises cutting an image capturing wafer to fabricate an image capturing portion having opposed surfaces defined by respective photodetection and reverse surfaces. The reverse surface includes external electrodes disposed thereon. Bonding the image capturing portion to a layered optical wafer having a plurality of optical wafers layered together. Cutting the layered optical wafer with the image capturing portion bonded thereto and fabricating an image capturing unit in which a layered optical portion includes a plurality of optical members layered together. The layered optical portion having a front surface and a rear surface that is opposite the front surface. The rear surface of the layered optical portion is bonded to the photodetection surface of the image capturing portion. The front surface is larger in area than the photodetection surface. The image capturing portion having a first aspect ratio L1/W1 equal to or smaller than 1.5 as a ratio between a length L1 thereof in optical axis directions and a width W1 thereof in directions perpendicular to the optical axis directions. The layered optical portion having a second aspect ratio L2/W2 equal to or larger than 2.0 as a ratio between a length L2 thereof in the optical axis directions and a width W2 thereof in the directions perpendicular to the optical axis directions.

A further aspect of the disclosed technology is directed to a method of manufacturing an image capturing module. The method comprises cutting an image capturing wafer to fabricate an image capturing portion having opposed surfaces defined by respective photodetection and reverse surfaces. The reverse surface includes external electrodes disposed thereon. Bonding the image capturing portion to a layered device wafer having a plurality of device wafers layered together. Cutting the layered device wafer with the image capturing portion bonded thereto and fabricating an image capturing unit in which a layered device includes a plurality of devices layered together. The layered device having a first principal surface and a second principal surface that is opposite the first principal surface. The rear surface of the image capturing portion is bonded to the first primary surface of the layered device. Bonding the photodetection surfaced of the image capturing unit to a layered optical wafer having a plurality of optical wafers layered together and cutting the layered optical wafer with the image capturing unit bonded thereto. Fabricating an image capturing module in which a layered optical portion includes a plurality of optical members layered together. The layered optical portion having a front surface to which light is applied and a rear surface that is opposite the front surface. The rear surface is bonded to the photodetection surface. The image capturing unit is bonded to the rear surface of the layered optical portion. The rear surface is larger in area than the photodetection surface and the first principal surface is larger in area than the photodetection surface and smaller in area than the rear surface.

In the method of manufacturing the image capturing module, the image capturing portion has a first aspect ratio L1/W1 equal to or smaller than 1.5 as a ratio between a length L1 thereof in optical axis directions and a width W1 thereof in directions perpendicular to the optical axis directions. The layered optical portion has a second aspect ratio L2/W2 equal to or larger than 2.0 as a ratio between a length L2 thereof in the optical axis directions and a width W2 thereof in the directions perpendicular to the optical axis directions. In the method of manufacturing the image capturing module of claim, the image capturing unit has a third aspect ratio L4/W1 equal to or smaller than 1.5 as a ratio between a length L4 thereof in the optical axis directions and the width W1 of a bonded surface of the image capturing portion in the directions perpendicular to the optical axis directions.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An image capturing module used in an endoscope comprising:
   an image capturing portion having opposed surfaces defined by respective photodetection and reverse surfaces, the reverse surface includes external electrodes disposed thereon;
   a layered optical portion having a front surface to which light is applied and a rear surface that is opposite the front surface, the rear surface being bonded to the photodetection surface, the layered optical portion having a plurality of optical members layered together; and
   a layered device having a first principal surface with joint electrodes disposed thereon and a second principal surface that is opposite the first principal surface, the first principal surface being bonded to the reverse surface, the joint electrodes being joined to the external electrodes, the layered device having a plurality of semiconductor devices layered together, wherein
   the first principal surface is larger in area than the photodetection surface and smaller in area than the rear surface.

2. The image capturing module of claim 1, wherein
   the rear surface is larger in area than the photodetection surface, the image capturing portion having a first aspect ratio L1/W1 equal to or smaller than 1.5 as a ratio between a length L1 thereof in optical axis directions and a width W1 thereof in directions perpendicular to the optical axis directions, the layered optical portion having a second aspect ratio L2/W2 equal to or larger than 2.0 as a ratio between a length L2 thereof in the optical axis directions and a width W2 thereof in the directions perpendicular to the optical axis directions.

3. The image capturing module of claim 1, wherein
   the rear surface is larger in area than the photodetection surface, the image capturing portion having a first aspect ratio L1/W1 equal to or smaller than 1.5 as a ratio between a length L1 thereof in optical axis directions and a width W1 thereof in directions perpendicular to the optical axis directions, the layered optical portion having a second aspect ratio L2/W2 equal to or larger than 2.0 as a ratio between a length L2 thereof in the optical axis directions and a width W2 thereof in the directions perpendicular to the optical axis directions.

4. The image capturing module of claim 3, wherein
   the layered optical portion has first side surfaces being defined as first cut surfaces.

5. The image capturing module of claim 1, wherein
   the rear surface is larger in area than the photodetection surface, the image capturing portion having a first aspect ratio L1/W1 as a ratio between a length L1 thereof in optical axis directions and a width W1 thereof in directions perpendicular to the optical axis directions, and a third aspect ratio L4/W1 as a ratio between a length L4 of an image capturing unit including the image capturing portion and the layered device, in the optical axis directions and the width W1 of the image capturing portion in the directions perpendicular to the optical axis directions, each of the first aspect ratio and the third aspect ratio being equal to or smaller than 1.5, the layered optical portion having a second aspect ratio L2/W2 equal to or larger than 2.0 as a ratio between a length L2 thereof in the optical axis directions and a width W2 thereof in the directions perpendicular to the optical axis directions.

6. The image capturing module of claim 5, wherein the layered optical portion has first side surfaces being defined as first cut surfaces and the layered device has second side surfaces being defined as second cut surfaces.

7. The image capturing module of claim 1, wherein the layered optical portion has corners substantially parallel to an optical axis thereof, the corners being beveled; and
the image capturing portion has third side surfaces disposed substantially parallel to beveled surfaces of the layered optical portion.

8. The image capturing module of claim 1, wherein the layered optical portion has corners substantially parallel to an optical axis thereof, the corners being beveled; and
the image capturing portion has third side surfaces disposed so as to cross at approximately 45 degrees to beveled surfaces of the layered optical portion.

9. The image capturing module of claim 1, wherein an auxiliary member is disposed on a region, to which the image capturing portion is not bonded, of the rear surface of the layered optical portion.

10. The image capturing module of claim 9, wherein the auxiliary member comprises a light shield resin covering side surfaces of the layered optical portion.

11. The image capturing module of claim 9, further comprising:
a frame member having a through hole in which the image capturing module is inserted and wherein
the auxiliary member includes a convex portion of a wall surface of the through hole.

12. A method of manufacturing an image capturing module, the method comprising:
cutting an image capturing wafer to fabricate an image capturing portion having opposed surfaces defined by respective photodetection and reverse surfaces, the reverse surface includes external electrodes disposed thereon;
bonding the image capturing portion to a layered optical wafer having a plurality of optical wafers layered together; and
cutting the layered optical wafer with the image capturing portion bonded thereto, fabricating an image capturing unit in which a layered optical portion includes a plurality of optical members layered together, the layered optical portion having a front surface and a rear surface that is opposite the front surface, the rear surface of the layered optical portion being bonded to the photodetection surface of the image capturing portion, wherein
the front surface is larger in area than the photodetection surface, the image capturing portion having a first aspect ratio L1/W1 equal to or smaller than 1.5 as a ratio between a length L1 thereof in optical axis directions and a width W1 thereof in directions perpendicular to the optical axis directions, the layered optical portion having a second aspect ratio L2/W2 equal to or larger than 2.0 as a ratio between a length L2 thereof in the optical axis directions and a width W2 thereof in the directions perpendicular to the optical axis directions.

13. A method of manufacturing an image capturing module, the method comprising:
cutting an image capturing wafer to fabricate an image capturing portion having opposed surfaces defined by respective photodetection and reverse surfaces, the reverse surface includes external electrodes disposed thereon;
bonding the image capturing portion to a layered device wafer having a plurality of device wafers layered together;
cutting the layered device wafer with the image capturing portion bonded thereto, fabricating an image capturing unit in which a layered device includes a plurality of devices layered together, the layered device having a first principal surface and a second principal surface that is opposite the first principal surface, the rear surface of the image capturing portion being bonded to the first primary surface of the layered device;
bonding the photodetection surfaced of the image capturing unit to a layered optical wafer having a plurality of optical wafers layered together; and
cutting the layered optical wafer with the image capturing unit bonded thereto, fabricating an image capturing module in which a layered optical portion includes a plurality of optical members layered together, the layered optical portion having a front surface to which light is applied and a rear surface that is opposite the front surface, the rear surface being bonded to the photodetection surface, the image capturing unit being bonded to the rear surface of the layered optical portion, wherein
the rear surface is larger in area than the photodetection surface, and the first principal surface is larger in area than the photodetection surface and smaller in area than the rear surface.

14. The method of manufacturing the image capturing module of claim 13, wherein
the image capturing portion has a first aspect ratio L1/W1 equal to or smaller than 1.5 as a ratio between a length L1 thereof in optical axis directions and a width W1 thereof in directions perpendicular to the optical axis directions, and the layered optical portion has a second aspect ratio L2/W2 equal to or larger than 2.0 as a ratio between a length L2 thereof in the optical axis directions and a width W2 thereof in the directions perpendicular to the optical axis directions.

15. The method of manufacturing the image capturing module of claim 14, wherein
the image capturing unit has a third aspect ratio L4/W1 equal to or smaller than 1.5 as a ratio between a length L4 thereof in the optical axis directions and the width W1 of a bonded surface of the image capturing portion in the directions perpendicular to the optical axis directions.

* * * * *